United States Patent [19]

Denes

[11] Patent Number: 4,620,000

[45] Date of Patent: Oct. 28, 1986

[54] METHOD FOR PREPARING 4-HYDROXYCINNOLINES IN A PH CONTROLLED SYSTEM

[75] Inventor: Lucian R. Denes, Modesto, Calif.

[73] Assignee: Shell Oil Company, Houston, Tex.

[21] Appl. No.: 737,963

[22] Filed: May 28, 1985

[51] Int. Cl.$^4$ .......................................... C07D 237/28
[52] U.S. Cl. .................................................. 544/235
[58] Field of Search ........................................ 544/235

[56] References Cited

PUBLICATIONS

Bersche and Herbert, *Annalen der Chemie,* vol. 546, pp. 293–303, (1944).

Leonard and Boyd, *J. Org. Chem.,* vol. 11, pp. 419–428, (1946).

Schofield and Simpson, *J. Chem. Soc.* (London), pp. 512–524, (1945).

Leonard, *Chem. Rev.,* vol. 37, pp. 269–286, (1945).

*Primary Examiner*—Donald G. Daus
*Assistant Examiner*—Stephen M. Kapner

[57] ABSTRACT

In the preparation of a 4-hydroxycinnoline wherein the diazonium salt of a 2-aminoacetophenone in aqueous solution is allowed to undergo cyclocondensation, the improvement that comprises maintaining the pH of the solution between about 4.0 and 8.5 during the cyclocondensation.

2 Claims, No Drawings

METHOD FOR PREPARING 4-HYDROXYCINNOLINES IN A PH CONTROLLED SYSTEM

BACKGROUND OF THE INVENTION 4-hydroxycinnolines are of interest as precursors for the preparation of biologically active materials, such as potential antimalarial drugs and herbicides.

One method for preparing them is that described by W. Borsche and A. Herbert, Annalen der Chemie, volume 546, pages 293-303 (1944): 4-hydroxycinnolines are prepared by diazotizing a 2-aminoacetophenone in an aqueous medium, removing excess nitrous acid, allowing the resulting solution of the diazonium salt to stand overnight, and then heating the solution until the diazonium salt has disappeared. The salt undergoes cyclocondensation,

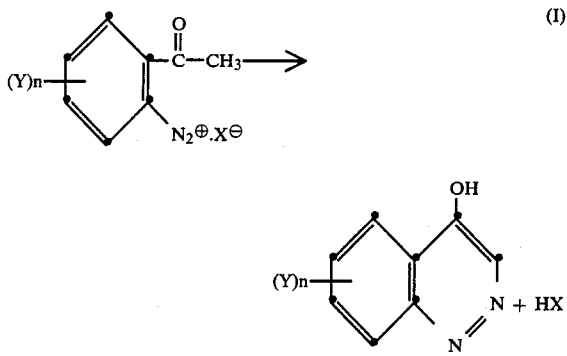

X being the anion of the acid used in the diazotization.

This general method was followed by N. J. Leonard and S. N. Boyd, Jr., in Journal or Organic Chemistry, volume 11, pages 419-428 (1946). They employed either water or aqueous acetic acid as the cyclocondensation medium, and did not heat the solution of the salt. Contemporaneously with their work, K. Schofield and J. C. E. Simpson, Journal of the Chemical Society (London), 1945, pages 512-520, prepared 4-hydroxycinnolines by the Borsche-Herbert method, except that they heated the solution of the diazonium salt, instead of holding it at room temperature. Messrs. Leonard and Boyd point out that while such a procedure accelerates the cyclocondensation, it markedly reduces the yield, while their procedure—holding the solution at room temperature—results in good yields. However, their procedure requires very long reaction times—of the order of 3 to 44 days.

It has now been discovered that good yields are obtained in much shorter times if the pH of the solution of the diazonium salt is maintained within a defined range while the cyclocondensation reaction is proceeding.

DESCRIPTION OF THE INVENTION

This invention provides an improvement in the known method for preparing 4-hydroxycinnolines by cyclocondensation of diazonium salts derived from corresponding 2-aminoacetophenones, in aqueous solution. The improvement comprises maintaining the pH of the solution within the range of from about 4.0 to about 8.5 during the time that the cyclocondensation is occurring.

Preferably, the pH of the solution is held within the range of from about 6.5 to about 8.0.

As is evident from the art, the basic method appears to be applicable to the preparation, generally, of 4-hydroxycinnolines from corresponding 2-aminoacetophenones. From the standpoint of the use of the 4-hydroxycinnolines as precursors for hericidal materials, the 4-hydroxycinnolines of interest are those wherein (referring to Formula I) n is zero, one, two, three or four, and Y is halogen, nitro, cyano or is alkoxy, alkylsulfonyl or alkoxycarbonyl of from one to six carbon atoms, or is alkyl of one to four carbon atoms substituted by one or more of the foregoing moieties, or is alkyl of one to six carbon atoms, or is phenyl.

The pH of the solution can be controlled within the desired range by monitoring the pH of the solution as the cyclocondensation reaction progresses, and adding an inert base, or preferably an aqueous solution of such, as the by-product acid, HX, is formed. Suitable bases include alkali metal bicarbonates, carbonates and hydroxides.

More conveniently, however, the pH of the solution is controlled within the desired range by adding a buffering agent at the outset, in an amount sufficient to maintain the pH within the desired range as the by-product acid is formed.

Suitable as the buffering agent is any of the materials commonly used for such a purpose and that is inert in the reaction mixture—suitable materials generally being water soluble salts of weak acids with strong bases. Examples are sodium acetate, potassium dihydrogen phosphate, dipotassium hydrogen phosphate and the like.

The amount of buffering agent used of course must be sufficient to maintain the pH of the solution within the desired range as the by-product acid is formed. Preferably, a moderate—i.e., ten to fifty percent—excess is used, as a precaution.

The buffering agent or an aqueous solution thereof can be added to the solution of the diazonium salt, or the solution of the salt can be added to an aqueous solution of the buffering agent.

The concentration of the diazonium salt in the buffered solution is not known to be critical. Suitably, the concentration of the salt in the solution is of the order of from about 0.1 molar to about 3 molar.

With the presence of the buffering agent, the temperature at which the cyclocondensation reaction is effected is less of a factor with respect to the yield of the 4-hydroxycinnoline. However, it appears best to treat the solution of the diazonium salt with the buffering agent, or aqueous solution thereof, at a low temperature, and then raise the temperature of the buffered solution if necessary. Accordingly, the cyclocondensation reaction can be carried out at any temperature above the freezing point of the solution, up to about 50° C. However, use of temperatures above about 30° C. does not appear to provide any significant advantage over use of lower temperatures, and such higher temperatures preferably are to be avoided to minimize the risk of undesired side-reactions.

Also, it has been found—and this finding forms a further, preferred aspect of the improvement provided by the invention—that the cyclocondensation reaction is further facilitated—yield can be improved, and isolation and purification of the 4-hydroxycinnoline product simplified—by including in the reaction mixture an essentially water-immiscible organic liquid that is a solvent for possible side-reaction products that may be formed and would themselves be reactive in the mixture to form other undesired by-products. Thus, diazonium salts tend to decompose to form phenols, which can react with the diazonium salt. Such phenols dissolve in the organic liquid phase, and thus are removed from the aqueous phase in which the salt is present. Generally, from about twenty-five to about fifty parts by volume of the organic liquid per one hundred parts by volume of the solution of the diazonium salt will be found to attain the desired objective.

Any essentially water-immiscible organic liquid that is a solvent for the phenol by-product and that is inert in the reaction mixture can be used. Preferably, to simplify isolation of the 4-hydroxycinnoline product, the liquid is one which the product is not soluble, or is soluble to a minimum extent. Typical materials of this kind are ethers, hydrocarbons, halogenated hydrocarbons and alkyl esters of lower alkanoic acids.

The progress of the cyclocondensation reaction can be followed by means of 2-naphthol spot tests—formation of a colored product indicates the existence of diazonium salt.

The 4-hydroxycinnoline product is insoluble in the aqueous phase of the reaction mixture, and preferably the organic liquid is chosen so that it is only a limited solvent for the product. In such case, the product separates out as a solid and is readily separated. Product that is dissolved in the organic liquid phase can be isolated by separating the organic phase, extracting it with an aqueous solution of a strong base, such as sodium hydroxide, then acidifying the extract with a strong non-oxidizing mineral acid, such as hydrochloric acid, as is illustrated in the examples, hereinafter.

Practice of the improvement of the invention in particular instances is illustrated in the following examples. In each case, the identities of the 4-hydroxycinnoline products and of any intermediates involved were confirmed by appropriate chemical and spectral analyses.

EXAMPLE 1

4-hydroxycinnoline (1)

28 g of 2-aminoacetophenone was added to a mixture of 35 ml of 37% hydrochloric acid, 80 ml of water and 80 g of ice. The resulting mixture was stirred while a solution of 13 g of sodium nitrite in 50 ml of water was added drop-by-drop, the rate of addition being adjusted so that the temperature of the mixture did not rise above 3° C. The mixture was stirred for a further hour at 3° C., about 1 g of urea was added and the resulting mixture was stirred at 30° C. until a negative test on iodine/starch paper was obtained.

The resulting diazonium salt solution was poured into a vigorously stirred mixture of 180 g of anhydrous sodium acetate, 500 ml of water and 250 ml of dichloromethane at 5° C. The resulting mixture was stirred for 7 hours, the internal temperature of the mixture being maintained at 10°–15° C., then stirred overnight at room temperature, and until the mixture gave a negative spot test with 2-naphthol. The resulting mixture was filtered, the collected solids were washed with cold water and dried in a vacuum oven (50° C./0.1 Torr) to give 1, m.p.: 228°–231° C. (Leonard and Boyd, 232°–233° C.). An analytical sample, recrystallized from ethanol, melted at 237° C. (Leonard and Boyd, 236° C.).

2.3 g of 1 was obtained by washing the dichloromethane phase with 1N aqueous sodium hydroxide solution (3×50 ml), then acidifying the combined alkaline extracts with concentrated hydrochloric acid.

EXAMPLE 2

5,8-dimethyl-4-hydroxycinnoline (2)

72.7 g of powdered iron was added over 130 minutes to a stirred suspension of 83.7 g of 3,6-dimethyl-2-nitroacetophenone (C. A. Howe and A. Howe, J. Chem. Soc., 1963, pp. 6064–6065) in 420 ml of water and 420 ml of glacial acetic acid, at room temperature. Then the mixture was heated to 35° C., when it became exothermic and the temperature rose slowly to 90° C. 10 grams of powdered iron was added and the mixture was stirred at 90–100° C. for 30 minutes. That procedure was repeated. The resulting mixture was cooled, quenched in water and the resulting mixture was filtered to remove the iron and extracted with ethyl acetate. The extract was washed successively with water, saturated aqueous sodium bicarbonate solution, water and brine, then dried (MgSO$_4$) and stripped of solvent. The residue was flash chromatographed over silica gel, using a 1:4 v:v mixture of ethyl acetate and hexane as eluent, to give 2-amino-3,6-dimethylacetophenone (2A), as a solid, m.p.: 156° C.

26.0 g of 2A was added to an ice-cold mixture of 70 ml of 12N hydrochloric acid and 30 ml of water. The mixture was stirred for 10 minutes, then 100 ml of water was added, followed by a solution of 11 g of sodium nitrite in 50 ml of water, added drop-by-drop over 20 minutes at about 0° C. The mixture was stirred for 15 minutes, then poured into an ice-cold mixture of 124 g of ice, 124 g of sodium acetate, 400 ml of water and 400 ml of methylene chloride. The mixture was stirred at 0°–5° C. for 3.5 hours, when it gave a negative reaction with beta-naphthol. The resulting mixture was filtered, the collected solids were dried under reduced pressure at room temperature overnight, recrystallized from ethyl acetate, and the product was dried in a vacuum oven at 40° C. over a weekend to give 2, as a tan solid, m.p.: 204°–205° C.

EXAMPLE 3

7,8-dimethyl-4-hydroxycinnoline (3)

22.3 ml of concentrated hydrochloric acid was added drop-by-drop to a stirred suspension of 2-amino-3,4-dimethylacetophenone (A. Brandstrom and S. A. I. Carlson, Acta Chemica Scandinavica, volume 21, pages 983–992 (1967)), 100 ml of water and 100 g of ice at 0° C. The resulting mixture was stirred at 0° C. for 15 minutes, then a solution of 7.8 g of sodium nitrite in 60 ml of water was added drop-by-drop over 2 minutes, at 0° C. The mixture was stirred for 40 minutes at 0° C., then 200 ml of ice-cold methylene chloride and 200 ml of an ice-cold aqueous solution containing 81.5 g of sodium acetate were added. The mixture was stirred for 6 hours at 0° C., allowed to warm gradually to room temperature, then filtered. The collected solid material was azeotroped with toluene and recrystallized from ethanol-hexane to give 3, as a tan solid, m.p.: above 260° C.

EXAMPLE 4

6,7-dimethyl-4-hydroxycinnoline (4)

95 ml of acetic anhydride was added to a stirred solution of 3,4-dimethylaniline in 300 ml of glacial acetic acid at such a rate the temperature of the mixture slowly rose to 60° C. The resulting mixture was stirred while the temperature dropped to room temperature, then evaporated to dryness. A mixture of water and ice was added to the residue, followed by methylene chloride. The resulting mixture was stirred and treated with solid sodium bicarbonate until neutral. The organic phase was separated, and dried ($MgSO_4$), and the solvent was evaporated to give 3,4-dimethylacetanilide (4A).

105 ml of acetyl chloride was added to a solution of 130 g of 4A in 1040 ml of carbon disulfide, then 410 g of aluminum chloride was slowly added to the stirred mixture. The mixture was stirred at reflux for 1.5 hours, cooled and the carbon disulfide phase was decanted. The remainder was poured onto ice, and the resulting precipitate was collected, washed with water and dried to give 2-acetyl-4,5-dimethylacetanilide (4B).

A mixture of 44 g of 4B and 300 ml of concentrated hydrochloric acid was refluxed for 30 minutes, then cooled in an ice bath and filtered. The collected solids were partitioned between methylene chloride and a saturated aqueous solution of sodium bicarbonate. The methylene chloride phase was separated and dried ($MgSO_4$), and the solvent was evaporated under reduced pressure. The residue was recrystallized from a 2:1 v:v mixture of hexane and ethyl acetate to give 2-amino-4,5-dimethylacetophenone (4C).

10.5 g of 4C was dissolved in 30 ml of concentrated hydrochloric acid kept cold with an ice bath, then 50 ml of water was added and the resulting mixture was treated at about 0° C. with sodium nitrite until the diazotation was complete by iodine-starch reaction. The resulting mixture was poured onto an ice-cold mixture of 50 g of sodium acetate, 150 ml of water, 50 g of ice and 50 ml of methylene chloride, and the mixture was stirred overnight, spontaneously warming to room temperature. The resulting mixture was filtered, the collected solid was washed with methylene chloride, then water, and dried in a vacuum oven. The product was recrystallized from ethanol to give 4, as orange crystals, m.p.: above 260° C. Further 4 was obtained by adding petroleum ether to the mother liquor from the recrystallization.

EXAMPLE 5

4-hydroxy-8-methoxycinnoline (5)

50.0 g of 3-methoxyacetophenone was slowly added drop-by-drop to 250 ml of 70% nitric acid at room temperature. After 17 hours, the resulting solution was warmed to 40° C. and held for one hour. The mixture was cooled, diluted with three times its volume of water and extracted with ethyl acetate. The extract was washed with water, then brine, dried ($NaSO_4$), and the solvent was evaporated. The residue was dissolved in ethyl acetate. Hexane was added and the mixture was set in dry ice. The solid material that formed was separated and dried under reduced pressure, to give 3-methoxy-2-nitroacetophenone (5A), as a cream colored solid, m.p.: 125°-127° C.

16.35 g of 5A was suspended in 220 ml of a 1:1 v:v mixture of ethyl acetate and water. 18.9 g of iron filings was added in portions over about 30 minutes. The resulting mixture was refluxed for 1.5 hours, diluted with water and extracted with ethyl acetate. The extract was washed with water, sodium carbonate solution, water, brine, dried ($Na_2SO_4$), and the solvent was evaporated. The residue was chromatographed over silica gel using a 1:1 v:v mixture of ethyl acetate and hexane as eluent.

One set of fractions was collected and stripped. The residue was dissolved in ethyl acetate, part of which then was evaporated, and the remainder was allowed to stand at room temperature. Solid material that formed was separated to give 2-amino-3-methoxyacetophenone (5B), as a pale green solid, m.p.: 61.5°-63° C.

3.30 g of 5B was suspended in a mixture of 20 ml of water, 20 g of ice and 4.5 ml of concentrated hydrochloric acid. Then, at 0° C., a solution of 1.45 g of sodium nitrite in 10 ml of water was added. After 25 minutes, 40 ml of chilled methylene chloride and a solution of 16.40 g of sodium acetate in 40 ml of water was added. The resulting mixture was stirred at about 12° C. overnight and filtered. The filtrate was dried under reduced pressure, then the solvent was evaporated to give 5, as a brown solid, m.p.: 160°-163° C.

EXAMPLE 6

8-ethoxy-4-hydroxycinnoline (6)

54.7 g of potassium carbonate was added to a solution of 51.6 g of 3-hydroxyacetophenone in 450 ml of acetone, under nitrogen. The mixture was heated to reflux and a solution of 66.6 g of diethyl sulfate in 50 ml of acetone was added drop-by-drop. The procedure required 61.5 hours. The mixture then was refluxed for 7.5 hours, diluted with water, and the resulting mixture was extracted with ethyl acetate. The extract was washed with water, then brine, dried and stripped of solvent. The residue was chromatographed over silica gel, using a 4:1 v:v mixture of hexane and ethyl acetate as eluent. The major fraction thus obtained was chromatographed on silica gel, using an 8:1 mixture of hexane and ethyl acetate as eluent. Three fractions were obtained. The most polar was discarded. The other two were combined and distilled in a Kugelrohr apparatus; two fractions, 100° C., 1.5 Torr. (6A) and 100° C., 0.5 Torr. (6B), respectively, were identified as 3-ethoxyacetophenone.

53.0 g of 6B was added drop-by-drop over 4 hours to 250 ml of 70% nitric acid. The resulting mixture was diluted to three times its volume with water, and extracted with ethyl acetate. The extract was washed with water, then aqueous sodium carbonate solution, dried ($MgSO_4$) and stripped of solvent. The residue was dissolved in ethyl acetate, the solution was evaporated to 125 ml, and hexane was added. Solid material that formed was collected to give 3-ethoxy-2-nitroacetophenone (6C), as a solic, m.p.: 107°-108.5° C.

3.0 g of 6C was dissolved in 30 ml of a 1:1 v:v mixture of water and acetic acid. 2.4 g of iron filings was added in portions over 30 minutes. The mixture was stirred for 1.5 hours, then at 60° C. for 2 hours. 1.0 g of iron filings was added and the mixture was stirred for 1 hour at 60° C., then filtered. The organic phase was washed with water, dried ($Na_2SO_4$) and stripped of solvent. The residue was chromatographed over silica gel, using ethyl acetate as eluent, to give 2-amino-3-ethoxyacetophenone (6D).

6.6 g of 6D was mixed with 30 ml of water and 30 g of ice. 8.3 ml of concentrated hydrochloric acid was added, followed 15 minutes later by another 1.7 ml. After a few minutes, the mixture was allowed to come to room temperature and another 3 ml of concentrated hydrochloric acid was added. When all of the solid material had dissolved, the mixture was cooled and, at 0° C., 2.6 g of sodium nitrite was added. After 1 hour, 30 ml of cold methylene chloride and a solution of 50.1 g of sodium acetate trihydrate in 100 ml of water was added.

The mixture was stirred overnight at about 8° C. and the organic phase was separated, washed with brine, dried (Na$_2$SO$_4$) and stripped of solvent. The residue was dissolved in methylene chloride, and the solution was extracted with 1N aqueous sodium hydroxide solution. The extract was made acid (to pH=2) with concentrated hydrochloric acid, and the resulting solution was extracted with methylene chloride. The extract was washed with water, dried (Na$_2$SO$_4$), and stripped of solvent. The residue was chromatographed over silica gel, using a 1:1 v:v mixture of hexane and ethyl acetate as eluent, to give 6, as a salmon-colored solid, m.p.: 161°–164° C.

EXAMPLE 7

5,8-dimethoxy-4-hydroxycinnoline (7)

2-amino-3,6-dimethoxyacetophenone (7A) was prepared by reduction of 3,6-dimethoxy-2-nitroacetophenone (C. A. Howe, et al., Journal of Organic Chemistry, volume 27, pages 1923–1925 (1962)) with iron filings as described in Example 2 for the preparation of 2A from the corresponding nitroacetophenone.

25.2 ml of 12N hydrochloric acid was added to a stirred suspension of 20.2 g of 7A, 120 ml of water and 120 g of ice. The mixture was stirred for 30 minutes at 0° C., then a solution of 8.0 g of sodium nitrite in 65 ml of water was added drop-by-drop rapidly. The mixture was stirred at 0° C. for 30 minutes, then 210 ml of methylene chloride, and 210 ml of water containing 90.0 g of sodium acetate were added. The resulting mixture was stirred for 6 hours at 0° C., allowed to warm slowly to room temperature and stirred at room temperature overnight. The mixture gave a negative beta-naphthol test for diazonium salt. The mixture was filtered, the solid product dried under reduced pressure, washed with methylene chloride and dried under low pressure (0.1 Torr.) and room temperature to give 7, as a brick-colored solid, m.p.: 208°–210° C.

I claim:

1. In a method for the preparation of a 4-hydroxycinnoline wherein the diazonium salt of a 2-aminoacetophenone in aqueous solution is allowed to undergo cyclocondensation, the improvement that comprises conducting the cyclocondensation in the presence of a buffering agent and an essentially water-immiscible organic liquid, maintaining the pH of the solution between about 4.0 and 8.5.

2. The improvement according to claim 1 wherein the buffering agent is sodium acetate.

* * * * *